US00PP32623P2

(12) United States Plant Patent
Grazzini

(10) Patent No.: US PP32,623 P2
(45) Date of Patent: Dec. 15, 2020

(54) ***SYRINGA* PLANT NAMED 'G13099'**

(50) Latin Name: *Syringa vulgaris*
Varietal Denomination: G13099

(71) Applicant: Richard A. Grazzini, Bellefonte, PA (US)

(72) Inventor: Richard A. Grazzini, Bellefonte, PA (US)

( * ) Notice: Subject to any disclaimer, the term of this patent is extended or adjusted under 35 U.S.C. 154(b) by 0 days.

(21) Appl. No.: 16/602,933

(22) Filed: Dec. 31, 2019

(51) Int. Cl.
*A01H 5/00* (2018.01)
*A01H 6/00* (2018.01)

(52) U.S. Cl.
USPC ..... Plt./248

(58) Field of Classification Search
USPC ..... Plt./248
See application file for complete search history.

*Primary Examiner* — Susan McCormick Ewoldt
(74) *Attorney, Agent, or Firm* — Panitch Schwarze Belisario & Nadel LLP

(57) ABSTRACT

A new and distinct variety of *Syringa vulgaris* plant, referred to by its cultivar name, 'G13099', is provided which forms light lavender colored flowers which are fragrant. Dark green colored foliage is formed. The new variety provides vegetation that is moderately vigorous and the growth habit is densely branched and compact. The new variety is well suited for providing attractive ornamentation in the landscape.

1 Drawing Sheet

Botanical/commercial classification:
Latin name—*Syringa vulgaris*.
Varietal denomination—'G13099'.

SUMMARY OF THE INVENTION

The new variety of *Syringa vulgaris* plant originated in a controlled breeding program in Bellefonte, Pa. during May 2009. The objective of the breeding program was the development of a series of *Syringa* cultivars with a faster production cycle, compact habits, and strong powdery mildew resistance. The new cultivar was created by cross-pollination wherein two parents were crossed which previously had been studied in the hope that they would contribute the desired characteristics. The female parent (i.e., the seed parent) was *Syringa* x *oblata* 'Betsy Ross' (not patented). The male parent (i.e., the pollen parent) was a non-patented unnamed breeder seedling.

The parentage of the new variety can be summarized as follows:

'Betsy Ross' x unnamed breeder seedling

The new cultivar was discovered and selected as a single flowering plant within the progeny of the progeny of the above stated cross-pollination during May 2013 in a controlled environment in Bellefonte, Pa.

It was found that the new variety of *Syringa* plant of the present invention possesses the following combination of characteristics:

(a) forms attractive, light lavender colored fragrant flowers,
(b) exhibits dark green-colored foliage,
(c) provides moderately vigorous vegetation, and
(d) displays densely branched and compact growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Betsy Ross' variety (i.e., the seed parent) displays white colored flowers and exhibits an upright growth habit, whereas the new variety displays light lavender colored flowers and exhibits a compact growth habit. In addition, the unnamed breeder seedling male parent (i.e., the pollen parent) displays lighter lavender colored flowers, exhibits a less densely branched and less upright growth habit compared to the new variety. Moreover, the new variety can be readily be distinguished from related similar non-parental varieties. For example, the 'Excel' variety (not patented) is the most similar commercially available cultivar and displays smaller floret size, has a lighter lavender flower color, typically blooms one week earlier and are less densely branched compared to the new variety.

The new variety has been found to undergo asexual propagation at Bellefonte, Pa. by softwood cuttings since May 2013. Asexual propagation by softwood cuttings at Bellefonte, Pa. has shown that the characteristics of the new variety are stable and are strictly transmissible by such asexual propagation from one generation to another. Accordingly, the new variety undergoes asexual propagation in a true-to-type manner.

The new variety has been named 'G13099'.

The new variety has not been sold or offered for sale at the time of filing the instant application.

BRIEF DESCRIPTION OF THE PHOTOGRAPHS

The accompanying photographs shows as nearly true as it is reasonably possible to make the same, in color illustrations of this character, typical specimens of the new variety.

The *Syringa* plants of the new variety were approximately five years old and growing in the ground in May at Cochranville, Pa.

The drawing sheet—illustrates a specimen the plant—side view—displaying the overall growth and flowering habit.

DETAILED BOTANICAL DESCRIPTION

The chart used in the identification of colors described herein is The R.H.S. Colour Chart of The Royal Horticultural Society, London, England, 2015 edition, except where general color terms of ordinary significance are used. The color values were determined in April 2020 under natural light conditions in Cochranville, Pa.

The following descriptions and measurements describe plants produced from cuttings from stock plants. The plants were grown outside in a field on their own roots for approximately five years. Measurements and numerical values represent averages of typical plants.

Class: *Syringa* Plant.

Propagation:

*Type cutting*.—Softwood cuttings.

*Time to initiate roots*.—Approximately 5 weeks.

*Time to produce a rooted cutting*.—Approximately 11 weeks.

*Root description*.—Fibrous and fine; white to brown in color.

*Rooting habit*.—Freely branching; dense.

Plant:

*Habit*.—Densely branched and compact.

*Commercial crop time*.—Approximately 10-11 months from a 4-inch liner to finish in a three-gallon container.

*Growth habit and general appearance*.—Flowering shrub, densely branched and compact growth habit.

*Hardiness*.—USDA Zone 4.

*Size*.—Height: approximately 135.0 cm. — width: approximately 180.0 cm.

*Branching habit*.—Freely branching. — quantity of branches per plant: approximately 7 main stems per plant with approximately 5 to 7 lateral branches per stem.

*Lateral branches*.—Strength: strong. — length: approximately 30.0 cm. — diameter: approximately 1.0 cm. — length of central internode: approximately 3.0 cm. — texture of mature stem: woody. — color of mature stems: commonly near Grey-Brown Group N199A.

Foliage:

*General description*.—Form: simple. — arrangement: alternate. — fragrance: none detected.

*Leaves*.—Aspect: 45° to stem. — shape: deltoid to orbicular. — margin: entire. — apex: acute. — base: truncate. — venation pattern: pinnate. — length of mature leaf: approximately 6.0 cm. — width of mature leaf: approximately 3.5 cm. — texture of upper and lower surfaces: glabrous. — color of upper surface of developing foliage: commonly near Yellow-Green Group 146A with venation of near Yellow-Green Group 146B. — color of lower surface of developing foliage: commonly near Yellow-Green Group 146B with venation of near Yellow-Green Group 146C. — color of mature foliage: commonly near Green Group NN137B with venation of near Green Group 137B. — color of lower surface of mature foliage: commonly near Green Group 138A with venation of near Green Group NN137D.

*Petiole*.—Length: approximately 2.0 cm. — diameter: approximately 2.0 mm. — texture: glabrous. — color of upper and lower surfaces: commonly near Yellow-Green Group144A.

Inflorescence:

*Lastingness of individual inflorescence on the plant*.—Approximately 7 to 10 days.

*Fragrance*.—Strongly fragrant; fragrance sweet and pleasant.

*Inflorescence height*.—Approximately 15.0 cm.

*Inflorescence diameter*.—Approximately 10.0 cm.

*Flower arrangement and flowering habit*.—Single salverform flowers arranged in terminal panicles; freely flowering habit with usually about 100 flowers per inflorescence; flowers face upright to slightly outwardly.

*Flowering season*.—Plants of the new *Syringa* plant flower in early spring in Cochranville, Pa.; flowers not persistent.

*Flower*.—Diameter: approximately 1.8 cm. — length (height): approximately 1.5 cm. — throat diameter: approximately 2.0 mm. — tube length: approximately 9.0 mm. — tube diameter, proximally: approximately 2.0 mm.

*Flower buds*.—Length: approximately 1.3 cm. — diameter: approximately 5.0 mm. — shape: obovate. — color: commonly near Violet Group 84A.

*Petals*.—Quantity and arrangement: single whorl of four to five petals; lower portion of petals fused forming a narrow tube. — lobe length: approximately 9.0 mm. — lobe width: approximately 5.0 mm. — lobe shape: ovate. — apex: obtuse to acute. — margin: entire. — texture, upper and lower surfaces: smooth, glabrous. — texture, throat and tube: smooth, glabrous. — color when opening and fully opened, upper and under surfaces: commonly near Violet Group 84A.

*Sepals*.—Quantity and arrangement: single whorl of four sepals; fused towards the base forming a campanulate-shaped calyx. — length: approximately 2.0 mm. — width: approximately 1.0 mm. — shape: narrowly deltoid. — apex: acute. — margin: entire. — texture, upper and lower surfaces: glabrous. — color, upper and lower surfaces: commonly near Yellow-Green Group 145A.

*Peduncles*.—Length: approximately 4.0 cm. — diameter: approximately 2.0 mm. — strength: strong. — aspect: about 45 degree to 90 degree from stem axis. — texture: smooth, glabrous. — color: commonly near Greyed-Green Group 197A.

*Pedicels*.—Length: approximately 4.0 mm. — diameter: approximately 1.0 mm. — strength: strong. — aspect: approximately 45 degree from peduncle axis. — texture: smooth, glabrous. — color: commonly near Green Group 143A.

*Reproductive organs*.—

*Androecium*.—Stamen quantity: 2 to 3 per flower. — stamen length: approximately 3.0 mm. — anther shape: oblong. — anther length: approximately 3.0 mm. — anther color: commonly near Yellow Group 2B. — pollen amount: moderate. — pollen color: commonly near Yellow Group 2C.

*Gynoecium*.—Pistil quantity: 1 per flower. — pistil length: approximately 2.0 mm. — stigma shape: club-shaped. — stigma length: less than 1.0 mm. — stigma color: commonly near Green-White Group 157D. — style length: approximately 2.0 mm. — style color: commonly near Green-White Group 157D. — ovary diameter: less than 1.0 mm. — ovary color: commonly near Green Group 143C.

*Seed and fruit production*.—Neither seed nor fruit production has been observed.

Development:

*Vegetation*.—Moderately vigorous.

*Tolerance to disease and pest resistance*.—Strongly resistant to lilac powdery mildew, plants of the new *Syringa* have not been observed to be resistant to pests common to *Syringa* plants.

The new 'G13099' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Syringa* plant characterized by the following combination of characteristics:

(a) forms attractive, light lavender colored fragrant flowers, (b) exhibits dark green-colored foliage, (c) provides moderately vigorous vegetation, and (d) displays densely branched and compact growth habit; substantially as herein shown and described.

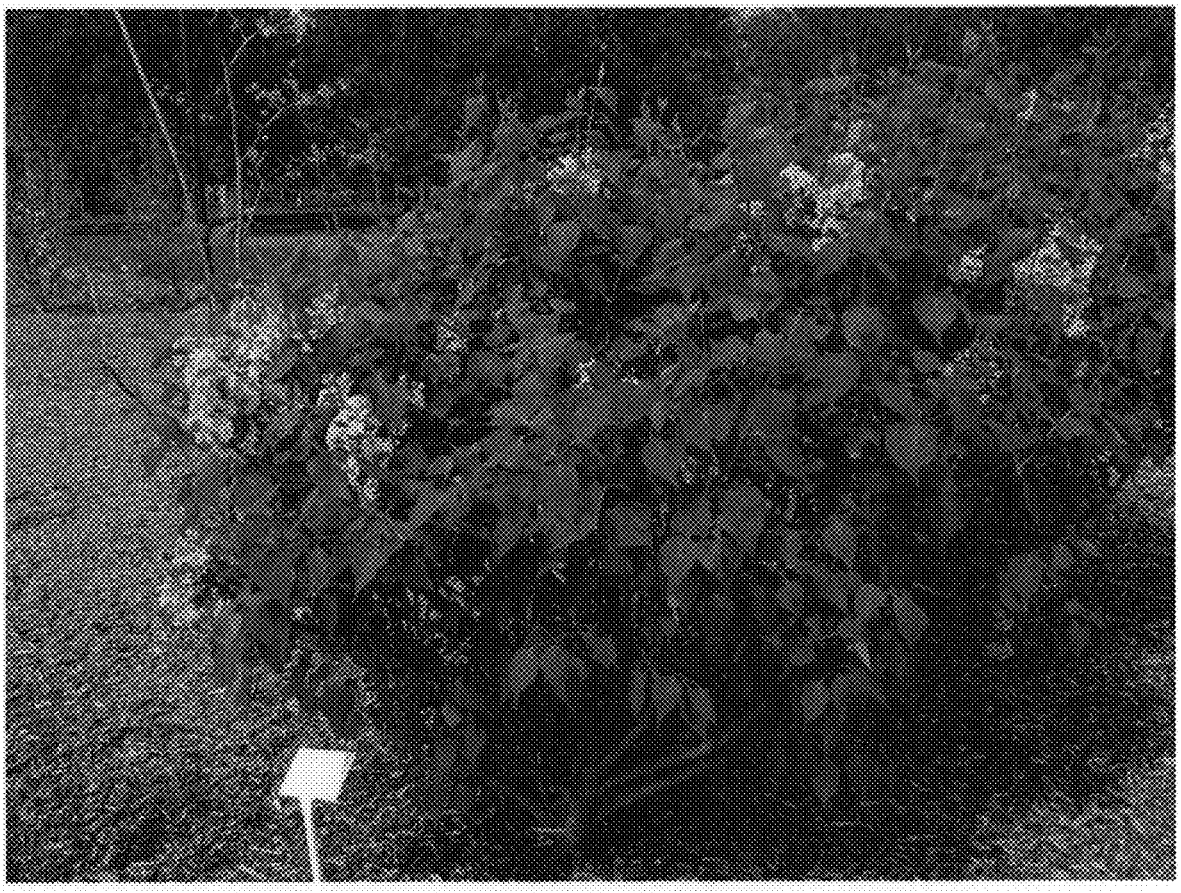

* * * * *